United States Patent [19]

Nagle

[11] 4,191,175

[45] Mar. 4, 1980

[54] METHOD AND APPARATUS FOR REPETITIVELY PRODUCING A NOISE-LIKE AUDIBLE SIGNAL

[76] Inventor: William L. Nagle, c/o Seidel Gonda & Goldhammer, P.C. 600 Three Penn Center, Philadelphia, Pa. 19102

[21] Appl. No.: 870,050

[22] Filed: Jan. 16, 1978

[51] Int. Cl.[2] .............................................. A61B 19/00
[52] U.S. Cl. .................................................. 128/1 C
[58] Field of Search ............... 128/1 C, 2.1 B; 331/78

[56] References Cited

U.S. PATENT DOCUMENTS

| 3,576,185 | 4/1971 | Schulz et al. | 128/1 C |
|---|---|---|---|
| 4,034,741 | 7/1977 | Adams et al. | 128/1 C |

FOREIGN PATENT DOCUMENTS 1088607  10/1967  United Kingdom ..................... 128/1 C

OTHER PUBLICATIONS

Faran "The General Radio Experimenter" vol. 36, No. 7, Jul., 1962, pp. 4–5, 331/78.

Primary Examiner—William E. Kamm
Attorney, Agent, or Firm—Seidel, Gonda, Goldhammer & Panitch

[57] ABSTRACT

A digital pulse generator and shift register repetitively produce bursts of digital pulses at a first adjustable repetition frequency. The repetition frequency of the pulses in each burst is also adjustable. A pink noise filter accentuates the lower burst frequency components near 7 hz and substantially attenuates all frequency components of the bursts above a first cut-off point near 10 Khz. A tunable band pass amplifier having a center frequency adjustable over a preselected range of frequencies optimally detectable by the average human ear accentuates the pink noise filter output near 2.6 Khz. The tunable amplifier drives an audible signal source with noise-like pulses of varying amplitudes and frequency components. A low pass amplifier may be connected to the pink noise filter to generate a train of pulses having a repetition frequency near 7 hz which pulses a light source in synchronism with the audible noise-like signal.

10 Claims, 4 Drawing Figures

METHOD AND APPARATUS FOR REPETITIVELY PRODUCING A NOISE-LIKE AUDIBLE SIGNAL

BACKGROUND OF THE INVENTION

The present invention is directed to a method and apparatus for producing a noise-like signal for inducing a hypnotic or anesthetic effect in a human being. The invention also has application in crowd control consciousness level training (biofeedback) and heart rate detection training (biofeedback). The invention may also be used in creating special musical effects.

The invention is particularly directed to the creation of a filtered repetitive noise-like signal alone or in combination with a repetitive visible signal. The audible signal has a pronounced effect on the human central nervous system.

Devices are known in the prior art for producing audible signals alone or in combination with a visible signal for inducing sleep. For example, see U.S. Pat. No. 3,576,185 to Shulz et al. which discloses a device for generating an audible pulsating sinusoidal signal and a visible signal in synchronism. Other devices which employ white noise sources for inducing sleep are also known. For example, see U.S. Pat. No. 3,835,833 to Limoge. Still other devices are known wherein sleep is induced by pulsing a light source at relatively low frequencies. See U.S. Pat. No. 3,388,699 to Webb et al. It is also known that the nervous system can be stimulated by amplitude modulated audible carrier signals at the alpha and theta frequencies of the brain. See U.S. Pat. No. 3,753,433 to Bakerich et al. (electroencephalophone feedback system).

None of these devices employ filtered repetitive noise-like audible signals to influence the human central nervous system. Such signals, however, are remarkably effective in changing states of consciousness or inducing hypnotic, anesthetic or sleep-like states.

An advantage of the invention is that it provides a filtered repetitive noise-like audible signal extremely effective in influencing the human central nervous system.

A further advantage of the invention is that it is versatile in that the audible signal frequencies can be adjusted to match the sensitivity of the central nervous systems of different individuals.

A further advantage of the invention is that it is of simple design and construction and relatively easy to trouble shoot and repair.

Other advantages appear hereinafter.

BRIEF SUMMARY OF THE INVENTION

Method and apparatus for repetitively producing a noise-like audible signal. Bursts of digital pulses are repetitively generated at a first frequency. The repetition frequency of the digital pulses within each burst is much higher than the burst frequency. The lower frequencies of the bursts near 7 hz are accentuated and the frequencies which lie above a first cut-off point are substantially attenuated by a pink noise filter. The frequencies of the bursts in an adjustable band pass preferably centered near 2.6 Khz are then accentuated by a tunable band pass amplifier. The output of the tunable band pass amplifier is a repetitive noise-like signal which drives an audible signal source. The 7 hz frequency component of the pulse bursts at the pink noise filter out-put may be further accentuated by a low pass amplifier which drives a light source.

For the purpose of illustrating the invention, there is shown in the drawings a form which is presently preferred; it being understood, however, that this invention is not limited to the precise arrangements and instrumentalities shown.

DETAILED DESCRIPTION OF THE INVENTION

Figure 1:
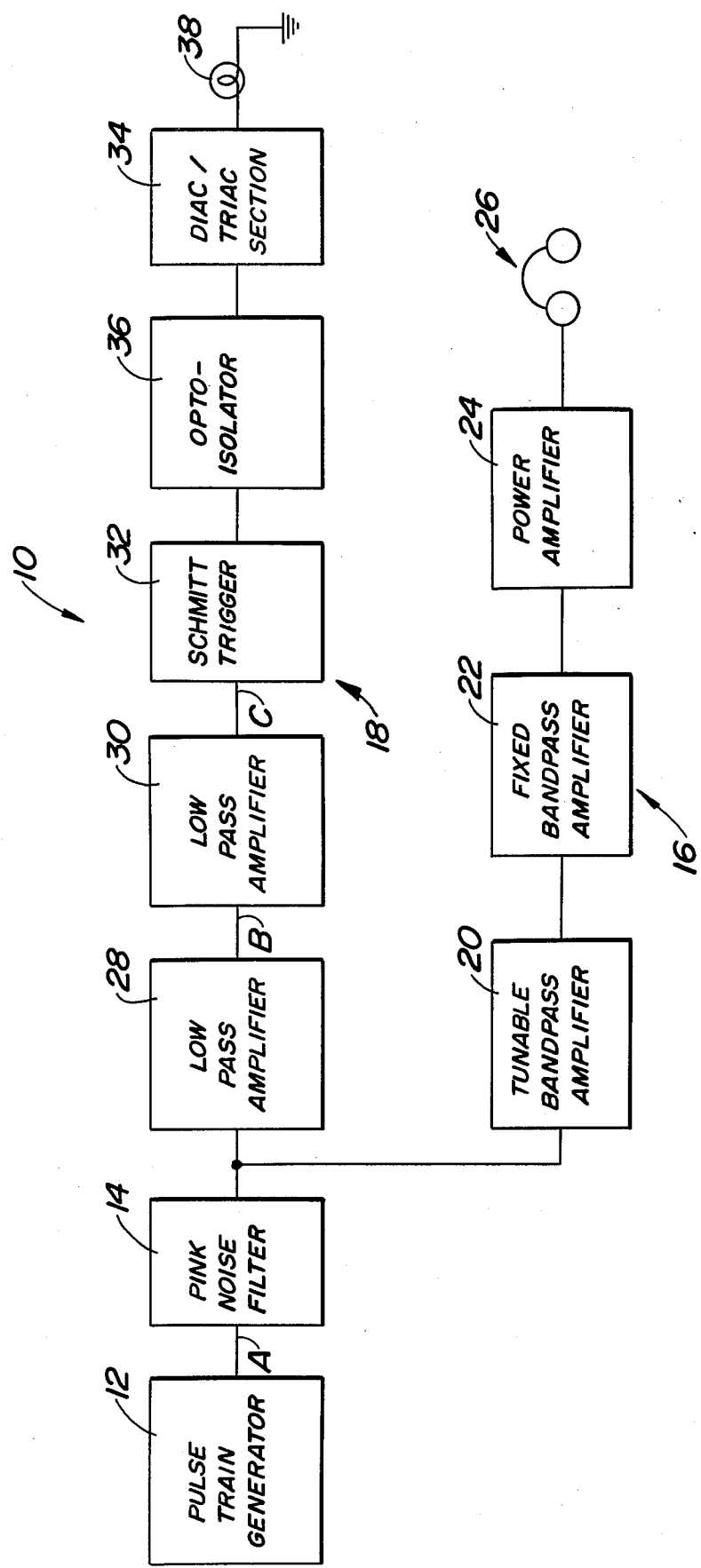
FIG. 1 is a block diagram of the apparatus of the present invention.
Figure 3:
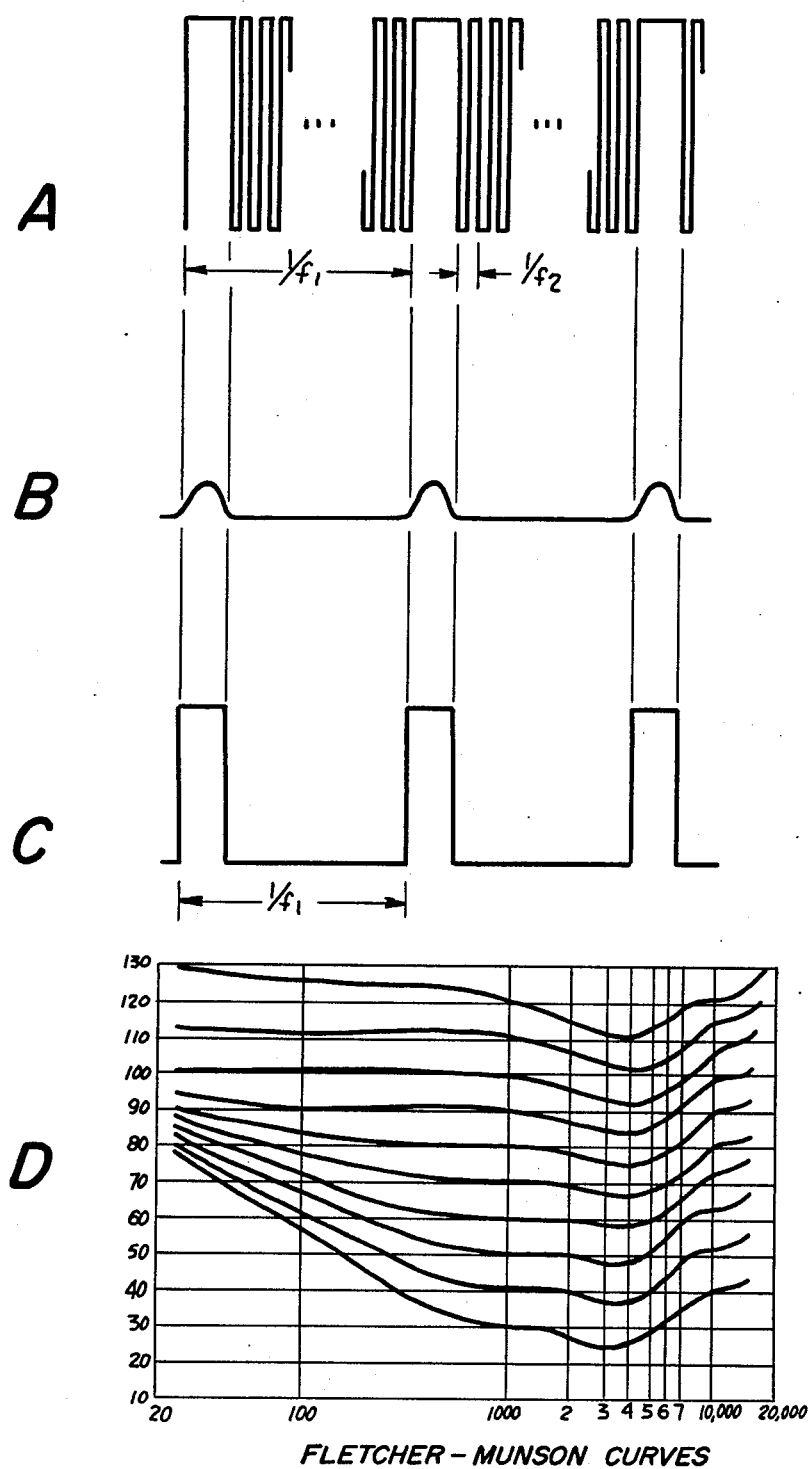
FIG. 3 is a diagram of certain waveforms produced by the apparatus.

Referring to FIG. 1, wherein like numerals indicate like elements, there is shown an apparatus 10 for generating a repetitive noise-like aubible signal alone or in combination with a visible signal for inducing a hypnotic, anesthetic or sleep-like state in an individual in accordance with the invention. A pulse train generator 12 repetitively generates bursts of digital pulses A. See FIGS. 1 and 3. Preferably, the repetition frequency of the bursts f1 is variable between approximately 0.5 hz and 12 hz. The repetition frequency f2 of the pulses within a burst is adjustable between approximately 15 Khz and 388 Khz.

The output of the pulse train generator 12 is passed through a pink noise filter 14 which is a relatively wide low pass filter. The pink noise filter 14 passes all frequencies between approximately 0 hz and 10 Khz, substantially attentuating all higher frequencies. For purposes of description herein, the 10 Khz frequency is regarded as the filter cut-off point.

The ouput of the pink noise filter 14 has a spectral content between approximately 0 hz and 10 Khz with the lower frequency components, preferably approximately 0 hz to 50 hz, being accentuated. This output signal is a repetitive noise-like signal having relatively narrow frequency band width compared to white noise. The output of the pink noise filter 14 is processed by an audible signal channel 16 and a visible signal channel 18. The audible signal channel 16 produces a repetitive noise-like signal having a frequency spectrum accentuated near 7 hz and 2.6 Khz as described more fully below. The visible signal channel 18 produces a relatively low frequency (near 7 hz) repetitive light signal which enhances the effect of the noise-like audible signal.

The audible signal channel 16 includes a tunable band pass amplifier 20 with an adjustable center frequency which is set between approximately 1.0 Khz and 7 Khz corresponding to the range of frequencies optimally detectable by the average human ear in accordance with the well-known Fletcher-Munson equal loudness contours. See FIG. 3.

The output of the tunable band pass amplifier 20 is passed through a fixed band pass amplifier 22 which as a fixed center frequency of approximately 2.6 Khz. The output of the fixed band pass amplifier 22 is amplified by a power amplifier 24. The power amplifier drives a pair of headphones 26 or other audible transducer such as a loudspeaker. The output of the power amplifier 24 is a repetitive noise-like signal consisting of a train of varying amplitude pulses. The spectral content of the noise-like signal at the output of amplifier 24 is accentuated at the 7 hz burst frequency and the 2.6 Khz center frequency. The signal includes the remaining frequencies passed by the pink noise filter 14 but attenuated according to the characteristics of the band pass amplifier. The noise-like signal has a unique spectral content which simulates audible noise or hiss roughly matched to the sensitivity of the average human ear.

The visible signal channel 18 includes a pair of low pass amplifiers 28 and 30. The low pass amplifier 28 passes all frequencies between approximately 0 hz and 65 hz, substantially attenuating all higher frequencies. Frequencies between approximately 0 hz and 20 hz are accentuated by the low pass amplifier 28. The output B of the amplifier is a repetitive pulse signal having rounded rising and falling edges. See FIG. 3. The output of the low pass amplifier 28 is shaped by low pass amplifier 30 to sharpen the rise and fall times of the pulses generated by amplifier 28 while preserving the accentuated frequency components between approximately 0 hz–20 hz. See waveform C in FIG. 3.

The output of low pass amplifier 30 drives a Schmitt trigger circuit 32. The Schmitt trigger circuit 32 squares the output of amplifier 30 and drives a conventional diac/triac section 34 via opto-isolator 36. The diac/triac section operates a light source 38 at approximately the 7 hz burst frequency.

If desired, the visible signal channel 18 may be omitted. It is preferred, however, that the individual be exposed to both the repetitive noise-like signal carried on earphones 26 as well as the relatively low frequency visible signal generated by light source 38.

Figure 2A:
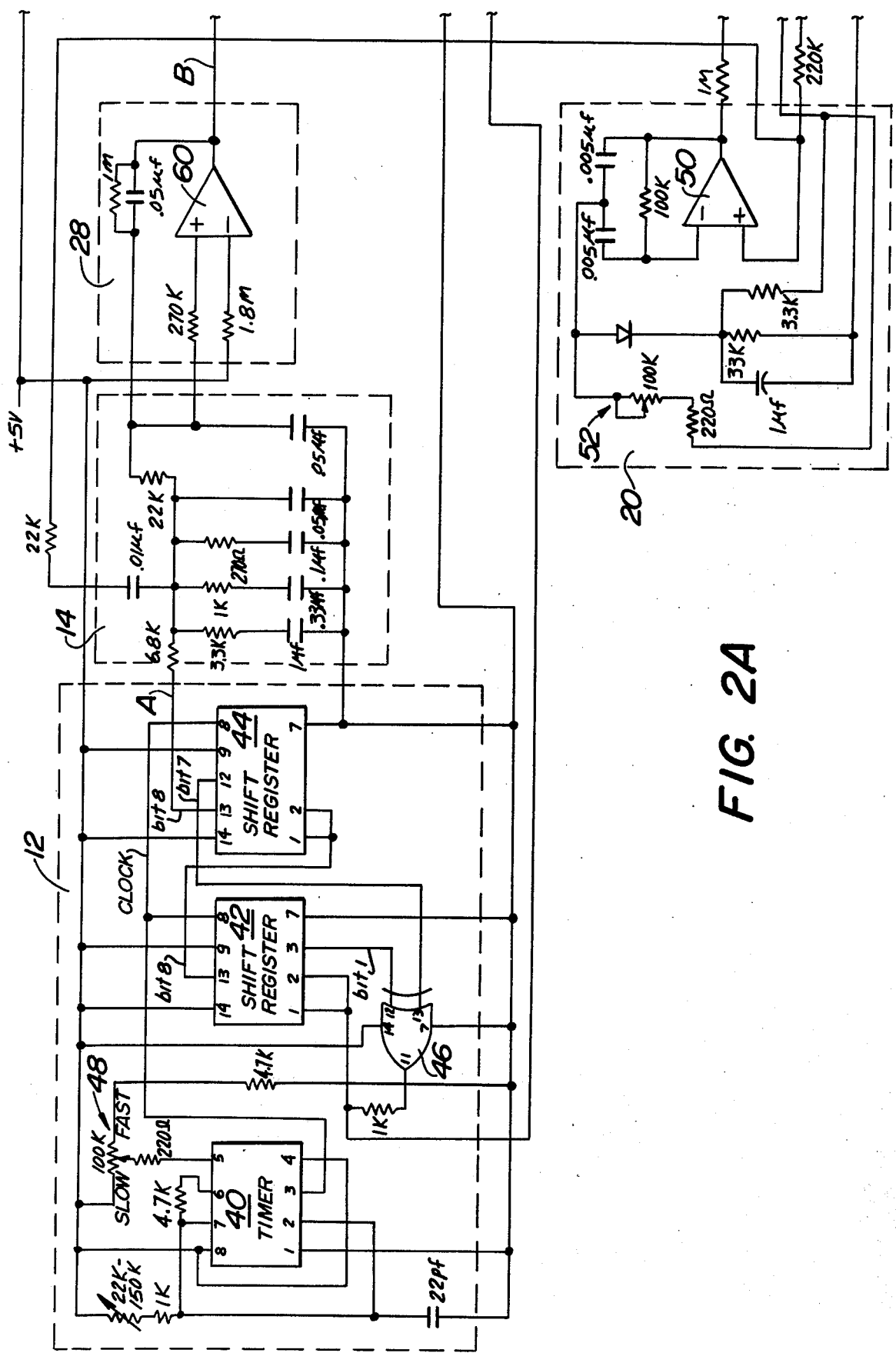
FIGS. 2A and 2B comprise an electrical schematic of the apparatus shown in FIG. 1.
Figure 2B:
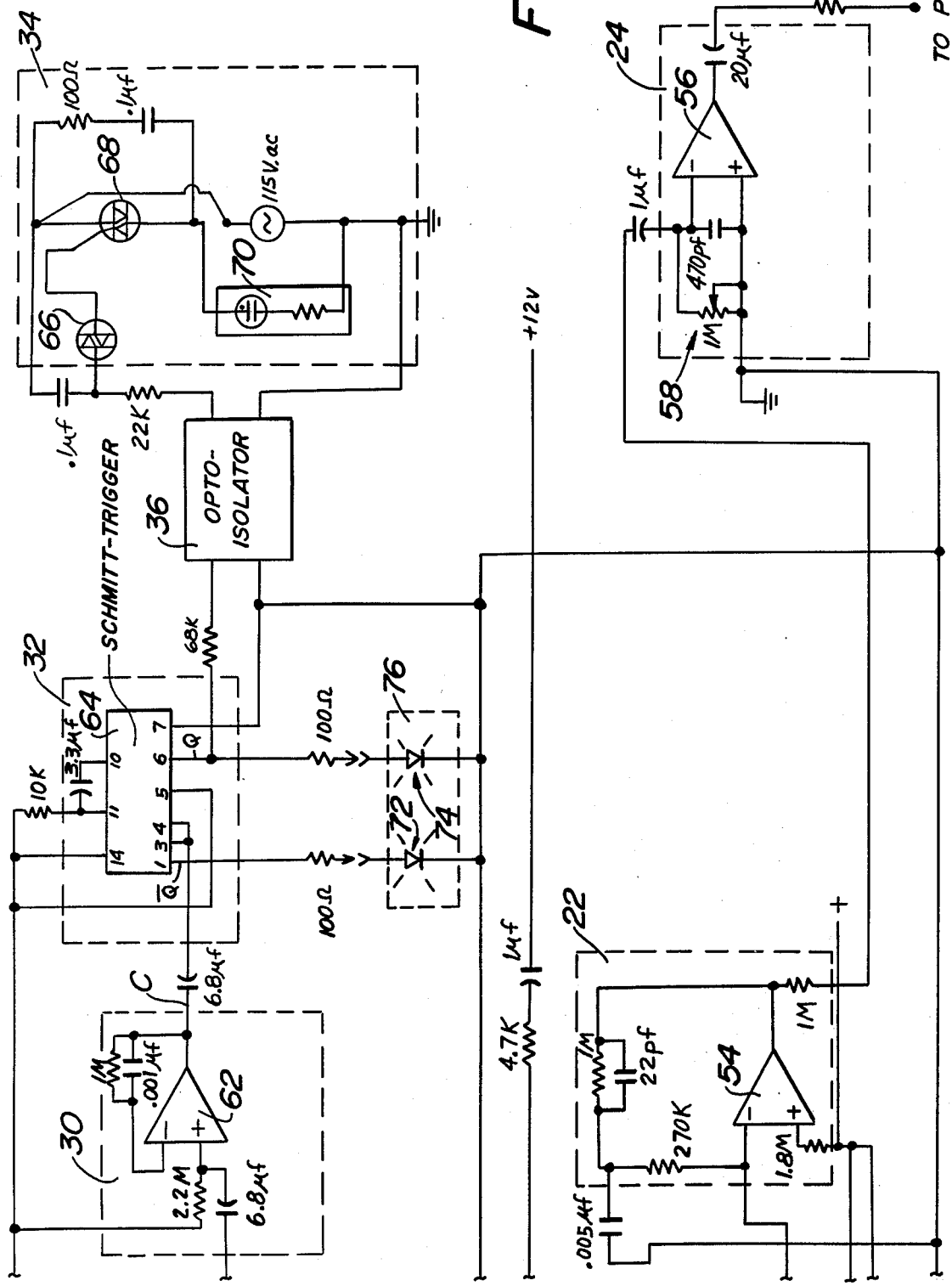

A preferred configuration of the electrical components shown in FIG. 1 is illustrated in FIGS. 2A and 2B. A precision timer 40 such as the SN 52555 timer is connected to operate in the astable mode. See FIG. 2A. Conventional pin numbers for the timer are designated within block 40. Pin 3 is the clock or output terminal.

The output of timer 40 clocks the shift registers 42 and 44. Shift registers 42 and 44 are SN 74164 8 bit parallel out serial shift registers connected in tandem to create a 16 bit register. Conventional pin numbers for the shift registers are designated within blocks 42 and 44. Pins 1 and 2 are the serial inputs. Pin 8 is the clock input. Pin 13 is the 8th or last bit of each shift register. Pin 12 is the 7th or next to last bit of each shift register. Pin 3 is the first bit of the shift register.

The first bit of shift register 42 and the 7th bit of register 44 are sensed by an Exclusive OR gate 46. Exclusive OR gate 46 may be a SN 7486 gate. Conventional pin numbers are designated within gate symbol 46.

The serial input to shift register 42 is regulated by the Exclusive OR gate 46. The gate 46 senses the first and 15th bits of the tandem shift register connection and toggles the serial input at the rate of the clock output from timer 40. When the first and 15th bits of the shift register are the same, the Exclusive OR gate 46 clamps the serial input of the shift register. As a result, the 8th bit of shift register 44 (the last bit of the tandem connection) does not change. This marks the end of each burst of pulses on line A. The clock output of timer 40 however, continues to shift data bits through the tandem connection. Eventually, bit 1 of shift register 42 and bit 8 of shift register 44 become complements and another burst of pulses is generated on line A. The timer 40 and shift registers 42 and 44 are free-running. Accordingly, the pulse bursts are continuously repeated at a regular rate (repetition frequency).

The repetition frequency of the pulses within each burst may be varied by means of a rate potentiometer 48. This has the effect of varying the repetition frequency of the clock output of timer 40 and, therefore, the frequency at which the bursts themselves are generated. The variation of the burst repetition frequency with the repetition frequency of the clock output of timer 40 is given in Table I below.

Table I

| Repetition Frequency f2 of Clock Output of Timer 40 in Khz | Repetition Frequency f1 of Pulse Bursts in hz |
|---|---|
| 15 | 0.5 |
| 163 | 5.0 |
| 182 | 5.5 |
| 195 | 6.0 |
| 215 | 6.5 |
| 230 | 7.0 |
| 250 | 7.5 |
| 266 | 8.0 |
| 293 | 9.0 |
| 333 | 10.0 |
| 364 | 11.0 |
| 388 | 12.0 |

The output of generator 12 is fed to the pink noise filter 14. The gain characteristic of the pink noise filter 14 shown in FIG. 2A is given in Table II below.

Table II

| Frequency in hz | Relative Gain (1 volt input) |
|---|---|
| 0–50 | 1.0 |
| 100 | 0.8 |
| 250 | 0.6 |
| 500 | 0.4 |
| 850 | 0.3 |
| 2000 | 0.2 |
| 6000 | 0.1 |

The output of the pink noise filter 14 is ac coupled to the input of tunable band pass amplifier 20 in the audible signal channel. In addition, the output of the pink noise filter is fed to the input of low pass amplifier 28 in the visible signal channel.

The tunable band pass amplifier 20 includes an operational amplifier 50 of the LM 3900 type or equivalent (such as the SN 72L044) connected as an active band pass filter. The tunable band pass amplifier has an adjustable center or peak frequency which may be shifted by means of a tune potentiometer 52. The gain of the amplifier as a function of the center frequency set by tune potentiometer 52 is given in Table III below.

Table III

| Center Frequency in hz | Relative Gain (1 volt input) |
|---|---|
| 600 | 0.8 |
| 1000 | 1.5 |
| 1500 | 2.2 |
| 2000 | 2.2 |
| 2600 | 2.9 |
| 3000 | 3.0 |
| 3500 | 3.2 |
| 4000 | 3.2 |
| 5000 | 3.4 |
| 6000 | 3.5 |
| 7000 | 3.5 |

The output of the tunable band pass amplifier 20 is fed to the fixed band pass amplifier 22 comprising an operational amplifier 54 of the LM 3900 type connected as an active band pass filter. The spectral characteristic of the fixed band pass amplifier is given in Table IV below:

Table IV

| Frequency in hz | Relative Gain (1 volt input) |
|---|---|
| 600 | 0.8 |
| 1000 | 1.8 |
| 1500 | 3.0 |
| 2000 | 3.0 |
| 2600 | 3.9 |
| 3000 | 3.2 |
| 3500 | 2.3 |
| 4000 | 1.6 |
| 5000 | 0.9 |
| 6000 | 0.5 |
| 7000 | 0.3 |

The center or peak frequency of the fixed band pass amplifier 22 is approximately 2.6 Khz. The 2.6 Khz frequency is of particular importance as it is within the most sensitive range of human hearing as indicated by the Fletcher-Munson equal loudness contours. See FIG. 3. A 2.6 Khz audible signal is known to induce strong physiological effects. See UCLA Weekly, Volume 7, No. 8 (Nov. 29, 1976) (2.6 Khz frequency produced by a whistling bottle). Accordingly, this frequency is emphasized in the repetitive noise-like signal generated at the output of band pass amplifier 22.

The output of band pass amplifier 22 is amplified by power amplifier 24. Power amplifier 24 includes an operational amplifier 56 of the LM 3900 type. The volume of the signal generated by amplifier 56 may be adjusted by means of a volume potentiometer 58.

The repetitive noise-like signal appearing at the output of amplifier 56 includes all frequency components between approximately 0 hz and 10 Khz (the nominal cut-off point of pink noise filter 14) with particular emphasis on the 2.6 Khz frequency. The signal includes the accentuated 7 hz burst frequency. The effectiveness of the signal in inducing physiological response is believed to be due to the noise-like nature of the signal which is simulated by the repetitive frequency components between approximately 0 hz and 10 Khz and the emphasized 2.6 Khz frequency. The signal simulates hiss having a spectral range corresponding to the Fletcher-Munson range (0 hz–10 Khz) with pronounced pulsating components near 2.6 Khz.

The output of the pink noise filter 14 may also be used to generate a low frequency light signal via the visible signal channel 18 as already indicated. The output of the pink noise filter is fed to the low pass amplifier 28 comprising an operational amplifier 60 of the LM 3900 type connected as an active low pass filter. The low pass filter 28 frequency characteristic is given in Table V below.

Table V

| Frequency in hz | Relative Gain (1 volt input) |
|---|---|
| 0–10 | 1.0 |
| 17 | 0.8 |
| 23 | 0.6 |
| 35 | 0.2 |
| 65 | 0.1 |

The low pass filter 28 accentuates the lower frequencies, 0 hz–20 hz. The 7 hz burst frequency is within the range of frequencies accentuated by the filter. The output of the filter is ac coupled to the second low pass amplifier 30 comprising an operational amplifier 62 of the LM 3900 type also connected as an active low pass filter.

Low pass amplifier 30 squares up the output of amplifier 28 to insure reliable operation of the Schmitt trigger circuit 32. The Schmitt trigger circuit 32 includes a SN 74121 monostable multivibrator 64 with Schmitt trigger input. Conventional pin numbers of the monostable multivibrator are designated in block 64. Pins 3, 4 and 5 are the inputs. Pins 10 and 11 are connected to the external timing circuit comprising the 10 K resistor and the 3.3 mf capacitor. Pin 6 is the Q output of the Schmitt trigger circuit. This output triggers the opto-isolator 36 at the 7 hz burst rate. The output of the Schmitt trigger circuit controls the diac/triac section 34 via the opto-isolator 36. Opto-isolator 36 may be a CLM 8000 type isolator.

The diac/triac section 34 includes a diac 66 which controls the gate of a triac 68. The triac alternately energizes and deenergizes a light source 70 (such as a neon tube) approximately at the 7 hz burst frequency. The low frequency light pulsations enhance the hypnotic or anesthetic effect produced by the noise-like audible signal generated by power amplifier 24.

The sensory effect produced by the noise-like audible signal and the low frequency light pulsations may be further enhanced by driving a pair of light emitting diodes 72 and 74 by the complementary outputs Q and Q of the Schmitt trigger circuit. The light emitting diode 72 and 74 may be secured in place in an eye shade 76 represented in phantom in FIG. 2B. The light emitting diodes are alternately pulsed, each at the 7 hz burst frequency.

The invention has been described in terms of various well-known electronic components such as precision timers, shift registers, Schmitt triggers and operational amplifiers. The invention is not limited to these particular devices but covers all equivalents thereof for attaining the same function and effect described herein.

As noted above, the generation of a repetitive noise-like signal in the audible signal channel having accentuated spectral components near 2.6 Khz entails a significant departure from prior art devices which employ broad band white noise generators or the like. By processing a repetitive burst of digital pulses through a pink noise filter and tunable and fixed band pass filters, the invention simulates a relatively narrow band noise (0 hz–10 Khz) with a strong component near 2.6 Khz.

It is preferred that the band pass amplifier 20 have a center frequency tunable over a range of frequencies corresponding to the most sensitive frequencies to the human ear as designated by the Fletcher-Munson curves. Preferably, the center frequency is tuned at approximately 2.6 Khz although other center frequencies including those between 1 Khz and 7 Khz may also be satisfactory. Assuming that the tunable band pass amplifier 20 is tuned to the 2.6 Khz center frequency, it will have a band pass characterisic as indicated in Table VI below.

Table VI

| Frequency in hz | Relative Gain (1 volt input) |
|---|---|
| 600–900 | 0.4 |
| 1800 | 0.6 |
| 2200 | 0.8 |

Table VI-continued

| Frequency in hz | Relative Gain (1 volt input) |
| --- | --- |
| 2600 | 1.0 |
| 3000 | 0.8 |
| 3200 | 0.6 |
| 3600 | 0.4 |
| 4500 | 0.2 |
| 6000 | 0.1 |

The band pass characteristic will vary somewhat as the center frequency is tuned to frequencies other than 2.6 Khz. The 2.6 Khz setting is, however, preferred for reasons already indicated.

The present invention may be embodied in other specific forms without departing from the spirit or essential attributes thereof and, accordingly, reference should be made to the appended claims, rather than to the foregoing specification as indicating the scope of the invention.

I claim:

1. Apparatus for repetitively producing a noise-like audible signal, comprising:
   an audible signal source,
   means for repetitively generating at a first adjustable repetition frequency bursts of digital pulses, said pulses within each burst having a second higher adjustable repetition frequency,
   pink noise filter means connected to said pulse burst generating means for substantially attentuating all frequencies of said repetitive bursts of digital pulses above a first cutoff frequency and for accentuating a preselected range of lower frequencies.
   tunable band pass filter means connected to said pink noise filter means for repetitively generating noise-like pulses of varying amplitudes, said tunable band pass filter means having a center frequency which is adjustable over a preselected range of frequencies which correspond to the frequencies optimally detectable by the average human ear, said noise-like signal having a frequency component accentuated at approximately said center frequency, and
   means connected to said tunable band pass filter means for driving said audible signal source.

2. The apparatus according to claim 1 including a light source and low pass filter means connected to said pink noise filter means for generating a train of pulses having a repetition frequency in the range of approximately 0.5 hz to 12 hz, and means connected to said low pass filter means for driving said light source at said 0.5 hz to 12 hz repetition frequency.

3. The apparatus according to claim 1 wherein said means for repetitively generating said bursts of digital pulses includes a digital pulse generator for generating a train of digital pulses at said second adjustable frequency, a shift register connected thereto, and a logical gate connected to said shift register for repetitively resetting said shift register at said first adjustable frequency.

4. The apparatus according to claim 3 wherein said pink noise filter means is a passive RC filter and said first cut-off frequency is approximately 10 Khz.

5. The apparatus according to claim 3 wherein said first adjustable frequency is approximately 7 hz, said second adjustable frequency is approximately 230 Khz, said preselected range of lower frequencies is approximately 0–50 hz, and said center frequency is approximately 2.6 Khz.

6. Apparatus for repetitively producing a noise-like audible signal, comprising:
   a light source and an audible signal source,
   means for repetitively generating at a first adjustable frequency bursts of digital pulses, said pulses within said burst having a second higher adjustable repetition frequency,
   pink noise filter means connected to said pulse burst generating means for substantially attenuating all frequencies of said repetitive bursts of digital pulses above a first cut-off frequency and for accentuating a preselected range of lower frequencies,
   tunable band pass filter means connected to said pink noise filter means for repetitively generating noise-like pulses of varying amplitude, said tunable band pass filter means having a center frequency which is adjustable over a preselected range of frequencies which correspond to the frequencies optimally detectable by the average human ear, said noise-like signal having a frequency component accentuated at approximately said center frequency,
   low pass filter means connected to said pink noise filter means for generating a train of pulses having a repetition frequency within said preselected range of lower frequencies, and
   means connected to said tunable band pass filter means and said low pass filter means for driving said light source with said train of pulses having a repetition frequency preselected range of lower frequencies and for simultaneously driving said audible signal source with said noise-like train of pulses.

7. A method of repetitively producing a noise-like audible signal, comprising:
   repetitively generating at a repetition first frequency bursts of digital pulses, said pulses within each burst having a second higher repetition frequency,
   generating a first repetitive signal based on said repetitive bursts of digital pulses wherein all frequencies of said repetitive bursts above a first cut-off frequency are substantially attenuated and a preselected range of lower frequencies is accentuated,
   generating a second repetitive noise-like signal based on said first repetitive signal wherein all frequencies within a preselected band pass within the range of frequencies optimally detectable by the average human ear are substantially accentuated, said second repetitive noise-like signal having a strong pulsating component at a preselected frequency within said band pass, and
   driving an audible signal source with said second repetitive noise-like signal.

8. The method according to claim 7 including generating a train of pulses based on said first repetitive signal having a frequency in the range of approximately 0.5 hz to 12 hz, and driving a light source with said train of pulses having a 0.5 hz to 12 hz repetition frequency.

9. The method according to claim 7 wherein said strong pulsating frequency component has a frequency of approximately 2.6 Khz.

10. A method of repetitively producing a noise-like audible signal, comprising:
    repetitively generating at a repetitive first frequency bursts of digital pulses, said pulses within each burst having a second higher repetition frequency,
    generating a first repetive signal based on said repetitive bursts of digital pulses wherein all frequencies of said repetitive bursts above a first cut-off frequency are substantially attenuated, and a preselected range of lower frequencies is accentuated generating a second repetitive noise-like signal based on said first repetitive signal wherein all frequencies within a preselected band pass within the range of frequencies optimally detectable by the average human ear are substantially acccentuated, said second repetitive signal having a strong pulsating component at a preselected frequency within said band pass, and generating a third repetitive signal based on said first repetitive signal having a frequency in the range of approximately 0.5 hz to 12 hz, and simultaneously driving a light source with said third repetitive signal and an audible signal source with said second repetitive noise-like signal.

* * * * *